United States Patent [19]

Beers

[11] Patent Number: 4,942,759

[45] Date of Patent: Jul. 24, 1990

[54] VISCOSITY TESTING APPARATUS

[75] Inventor: Howard L. Beers, North Fort Myers, Fla.

[73] Assignee: HF Scientific, Inc., Ft. Myers, Fla.

[21] Appl. No.: 401,030

[22] Filed: Aug. 31, 1989

[51] Int. Cl.⁵ ............................................. G01N 11/06
[52] U.S. Cl. ......................................................... 73/56
[58] Field of Search ................................ 73/55, 56, 54

[56] References Cited

U.S. PATENT DOCUMENTS

| | | | |
|---|---|---|---|
| 1,635,281 | 7/1927 | Larson | 73/56 |
| 1,659,534 | 2/1928 | Mason | 73/56 |
| 1,758,677 | 5/1930 | Smith | 73/56 |
| 2,419,658 | 4/1947 | Rogers | 73/55 X |
| 2,625,817 | 1/1953 | Oppenauer | 73/54 |
| 4,221,073 | 9/1980 | Malczewski | 73/56 X |
| 4,794,787 | 1/1989 | Gordon | 73/56 |

FOREIGN PATENT DOCUMENTS 2909373  9/1980  Fed. Rep. of Germany .......... 73/55

Primary Examiner—Hezron E. Williams
Assistant Examiner—Joseph W. Roskos
Attorney, Agent, or Firm—William E. Noonan

[57] ABSTRACT

A viscosity test apparatus is disclosed including a reference chamber that is partially filled by a predetermined volume of reference liquid having a known viscosity. There is a test chamber attached to the reference chamber which is partially filled with a test liquid having a volume and viscosity/temperature characteristic that are substantially similar to those of the reference liquid. An elongate first conducting column mounted within the reference chamber includes an open upper end that interconnects the reference chamber and the first column and a lower end having a first orifice that is submersible in the reference liquid for conducting the reference liquid under a pressure head between the first column and the reference chamber. A second column is mounted within the test chamber in substantial alignment with, and having dimensions substantially identical to the first column. The second column includes an open upper end and a lower end having a second orifice that is submersible in the test liquid for conducting the test liquid under a pressure head between the second column and the test chamber. The reference and test chambers are simultaneously manipulable to provide the liquids with respective pressure heads for driving the reference and test liquids respectively through the first and second orifices such that the levels of the reference liquid and the test liquid in the first and second column may be compared instantaneously to provide a measure of viscosity of the test liquid.

17 Claims, 4 Drawing Sheets

VISCOSITY TESTING APPARATUS

FIELD OF THE INVENTION

This invention relates to a viscosity testing apparatus and, in particular, to a submerged orifice, ascending/descending column viscosity tester that is especially suited for measuring the absolute and relative viscosity of hydrocarbon fuels.

BACKGROUND OF INVENTION

A number of devices are known for determining the viscosity of liquids. Most conventional viscometers require closely controlled conditions, such as those found in the laboratory, and are generally unsuited for use in the field. At times, however, field testing for viscosity may be required, for example, to determine if the fuel from captured or abandoned military vehicles is suitable for use. Such testing must be performed rapidly and accurately, often by relatively unsophisticated personnel, under a wide variety of temperature conditions. The test equipment is often subjected to rough handling. Unfortunately, prior techniques for measuring viscosity do not address these problems and have proven to be unduly time consuming, complicated and unreliable for use in the field.

One known method involves timing the descent of balls through respective columns containing liquids of varying viscosities. The apparatus used for this test requires extremely close tolerances. Even air bubbles can interfere with the descending balls and disrupt the test. To prevent the introduction of air into the liquid, the test chamber must be sealed. Nevertheless, the sealing gasket, which is often porous, tends to bleed. This may contaminate the liquid and invalidate the entire test. Moreover, the test balls can rattle such that the device is apt to crack or break when it is transported for use in the field.

A Cannon Fensky variety of viscometer requires timing the descent of a liquid column. This type of test requires a considerable amount of time, as well as close control over the test temperature. The completion of the test liquid's descent must be noted precisely. As a result, this technique requires sophisticated optical and electronic equipment.

Falling needle viscometers also require very close tolerances which can be disrupted by the presence of any debris or air bubbles in the test liquid. This mechanism, too, is highly sensitive to temperature fluctuations.

Rising bubble viscometers are also known. However, it is virtually impossible to control the size of the bubbles and, as a result, these mechanisms cannot provide an absolute measure of viscosity.

Drip cup viscometers involve timing a liquid stream from the orifice of a cup and noting the precise instant at which the stream converts to droplets. That point is often difficult and frustrating to discern. As a result, this test is often tedious and unreliable.

SUMMARY OF INVENTION

It is therefore an object of this invention to provide an improved viscosity testing device which operates rapidly, reliably and simply, without complicated or intricate parts, to provide very accurate measurements of liquid viscosity.

It is a further object of this invention to provide a viscosity tester that is accurate over a wide range of temperatures.

It is a further object of this invention to provide a viscosity tester that is particularly well suited for use in the field, even by relatively unsophisticated personnel.

It is a further object of this invention to provide a viscosity tester which enables both comparative and absolute viscosity testing to be performed.

This invention results from a realization that quick and extremely accurate measurements of liquid viscosity may be made by instantaneously comparing the relative levels of two or more similar columns of liquid, as the liquid in each column is driven by a respective pressure head through a submerged orifice in the column. Such an apparatus eliminates the need for close tolerances and intricate, sensitive moving parts.

This invention features a viscosity test apparatus that includes a reference chamber that is partially filled by a predetermined volume of a reference liquid having a known viscosity. There is a test chamber attached to the reference chamber and including means for partially filling the test chamber with a liquid having a volume and a viscosity/temperature characteristic that are substantially similar to those of the reference liquid. An elongate first conducting column is mounted within the reference chamber. The first column includes an open upper end that interconnects the reference chamber to the first column and a lower end having first orifice means that are submersible in the reference liquid for conducting the reference liquid under a pressure head between the first column and the reference chamber. The second conducting column is mounted within the test chamber in substantial alignment with the first column and has dimensions that are substantially identical to the first column. The second column includes an open upper end that interconnects the test chamber and the second column and a lower end that has second orifice means that are submersible in the test liquid for conducting test liquid under a pressure head between the second column and the test chamber. The reference and test chambers are simultaneously manipulable to provide the reference and test liquids with pressure heads for driving the reference and test liquids respectively through the first and second orifice means such that the respective levels of the reference liquid and the test liquid in the first and second columns may be compared instantaneously to provide a measure of viscosity of the test liquid.

In a preferred embodiment the reference chamber may be sealed and include a nitrogen atmosphere from which the oxygen has been substantially entirely removed. Each of the first and second columns may be tapered from its upper end to its lower end such that the liquid level in the column varies, under a pressure head, at a generally constant rate. The first and second orifice have substantially identical diameters. The reference chamber and the test chamber may include first and second transparent portions, respectively, for viewing the first and second columns. The first and second columns may include third and forth transparent portions, respectively, for viewing the instantaneous levels of the reference liquid and the test liquid in the first and second columns. The means for partially filling may include an entrance into the test chamber and means for selectively covering the entrance to hold the test liquid in the test chamber. The test and reference liquids may include various types of hydrocarbons. A standard chamber may be attached to at least one of the reference chamber and the test chamber. The standard chamber is partially filled by a standard liquid having a volume and a viscosity/temperature characteristic that is substantially similar to those of the reference liquid. A third conducting column may be mounted in the standard chamber in substantial alignment with the first and second columns. The third conducting column may have dimensions substantially identical to the first and second columns and, in particular, may include an open upper end that interconnects the standard chamber and the third column and a lower end having third orifice means that are submersible in the standard liquid for conducting standard liquid under a pressure head between the third column and the standard chamber. The standard chamber is simultaneously manipulable with the reference and test chambers to provide the reference, test and standard liquids with respective pressure heads for driving the reference, test and standard liquids through the first, second and third orifices, respectively, such that the levels of the liquids in the columns may be instantaneously compared to provide a measure of the viscosity of the test liquid relative to the reference and standard liquids.

The standard chamber may be sealed in a manner similar to the reference chamber. The second column may be tapered identically to the first and second columns and may include an orifice which is similar in size to that of the other columns. Likewise, the standard chamber and the third column may include respective transparent means for viewing the instantaneous level of the standard liquid in the third column. That liquid may include a hydrocarbon.

By comparing the descent of the test liquid down the second column with the descent of the reference and standard liquids down their respective columns, a comparative measure of viscosity is provided. Alternatively, an absolute measure of viscosity may be achieved. In such embodiments, the first and second columns are attached respectively to forward and rearward walls of the first and second chambers, such that one of the reference and test liquids descends under a pressure head within its respective column and the other of the reference and test liquids ascends under a pressure head. The reference and test chambers may include means for indicating when the respective fluid levels in the first and second columns are instantaneously equal to provide a measure of the absolute viscosity of the test liquid.

BRIEF DESCRIPTION OF THE DRAWINGS

Other objects, features and advantages will occur from the following description of preferred embodiments and the accompanying drawings, in which.

DETAILED DESCRIPTION OF PREFERRED EMBODIMENTS

Figure 1:
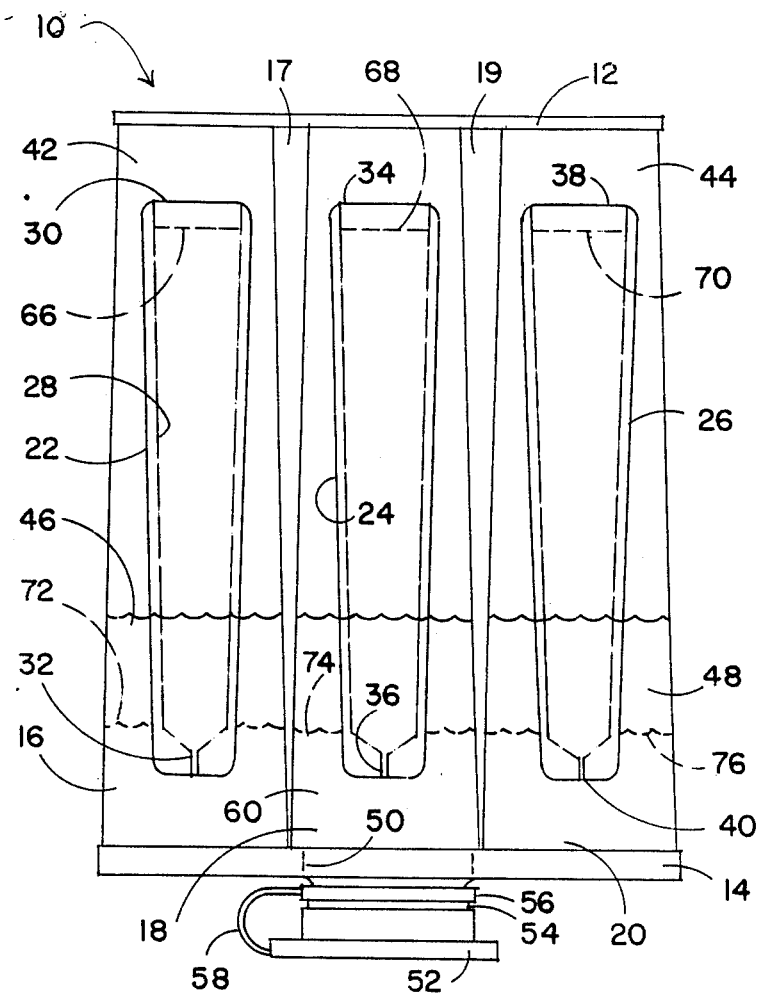
FIG. 1 is a front elevational view of a preferred viscosity tester according to this invention.

There is shown in FIG. 1 a viscosity test apparatus 10. The apparatus is composed of a sturdy, transparent plastic material such as polyetherimide. Such material is produced for example, under the trade name Ultem by General Electric. Polycarbonate, polystyrene and other lesser grades of material may also be used. That apparatus may be formed by molding or a similar process. Apparatus 10 includes a top 12, a bottom 14 and three adjoining reference, test and standard chambers 16, 18 and 20 extending between top 12 and bottom 14. Chamber 16 and chamber 18 are separated by a wall 17. Chamber 18 and chamber 20 are similarly separated by a wall 19. The chambers have identical sizes and may have circular, rectangular or various other cross sectional shapes.

Figure 2:
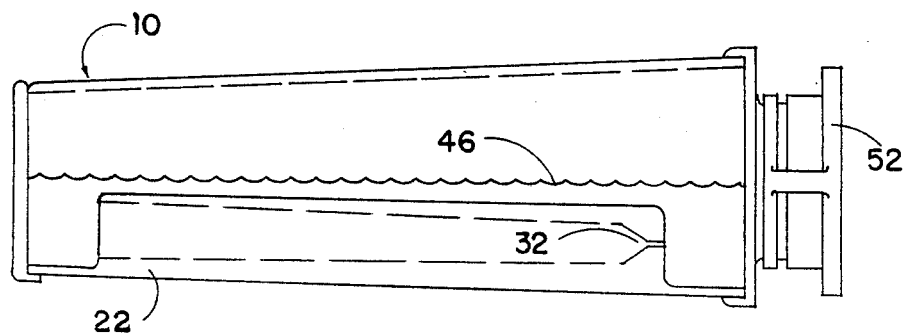
FIG. 2 is a side view of the viscosity tester of FIG. 1 being manipulated to fill the columns with respective liquids.

First, second and third elongate conducting columns 22, 24 and 26 are permanently mounted in chambers 16, 18 and 20, respectively. Each column includes a transparent material such as a clear plastic which is resistant to shock and breakage. As shown in FIG. 2, each of the columns, for example column 22, is attached to the rear wall of its respective chamber. Apparatus 10 may be integrally constructed, such as by molding. Alternatively, each column may be attached within its respective chamber by various welding or adhesive techniques. The dimensions of columns 22, 24 and 26 are substantially identical. Each column has an elongate, tapered conducting channel 28 that extends completely through the column. First column 22 has an open upper end 30 that interconnects channel 28 of column 22 with chamber 16 and a first orifice 32 that is formed at the lower end of the column. Second column 24 has a similar open upper end 34 and an orifice 36 that is disposed at its lower end. Likewise, third column 26 includes an open upper end 38 and an orifice 40 at its lower end. Preferably each of the orifices 32, 36 and 40 has an equal diameter that permits liquid to pass between the chamber and the column in a conveniently measurable period of time.

Reference chamber 16 is sealed and contains a nitrogen atmosphere 42 from which the oxygen has been substantially entirely removed. Standard chamber 20 is similarly sealed and includes a nitrogen atmosphere 44. Chamber 16 is partially filled by a predetermined volume of a reference liquid 46 which is typically a member of the same class as the liquid to be tested. That is, the reference liquid 46 and the test liquid 60 (which is added to chamber 18 as described below) have the same temperature/viscosity relationship. For example, if the test is being used to determine the viscosity of a hydrocarbon, a hydrocarbon is employed as reference liquid 46. Standard chamber 20 is likewise partially filled by the same predetermined volume of a standard liquid 48 having a viscosity/temperature characteristic that is substantially similar to that of the reference liquid. The viscosity of liquid 48 is also known. Typically, reference liquid 46 has a low viscosity and standard liquid 48 has a high viscosity. These two viscosities represent the upper and lower viscosity boundaries for the liquid to be tested.

Test chamber 18 is not sealed. Rather, it includes an entrance 50 that is selectively covered by a cap 52. The cap is attached to a lip 54, which surrounds entrance 50. A ring 56 surrounds the lip and a strap 58 interconnects ring 56 and cap 52. Chamber 18 may be partially filled with a test liquid 60 by removing cap 52 from over entrance 50 and introducing liquid 60 through the entrance.

To perform viscosity testing in accordance with this invention, chamber 18 is partially filled by liquid 60 to a level which is generally the same as the liquid levels in chambers 16 and 20. Liquid 60 has an unknown viscosity but a viscosity/temperature characteristic that is substantially similar to that of the reference liquid 46 and the standard liquid 48. When apparatus 10 is intended for use in testing hydrocarbons, liquids 46 and 48 will typically comprise such hydrocarbons. Prior to conducting the test, the apparatus is placed upright, as shown in FIG. 1, so that the levels of liquids 46, 60 and 48 are substantially identical. Within each chamber, the liquid level is constant, both inside and outside of the respective columns.

After test liquid 60 is introduced, the operator allows the temperatures of the respective liquids to equalize. Then, apparatus 10 is tipped generally horizontally, as shown in FIG. 2, so that columns, 22, 24 and 26 are submerged by the respective liquids 46, 60 and 48 within chambers 16, 18 and 20. Apparatus 10 is then manipulated back into a generally vertical position. As a result, liquid 46 generally fills column 22 as indicated by phantom level line 66. Similarly, liquid 60 in test chamber 18 generally fills second column 24, as indicated by level line 68; and standard liquid 48 generally fills third column 26, as indicated by level line 70. The liquid levels within the respective chambers 16, 18 and 20 drop to the levels indicated by lines 72, 74 and 76. The respective orifices 32, 36 and 40 remain submerged beneath the liquid in the chambers 16, 18 and 20.

Figure 3:
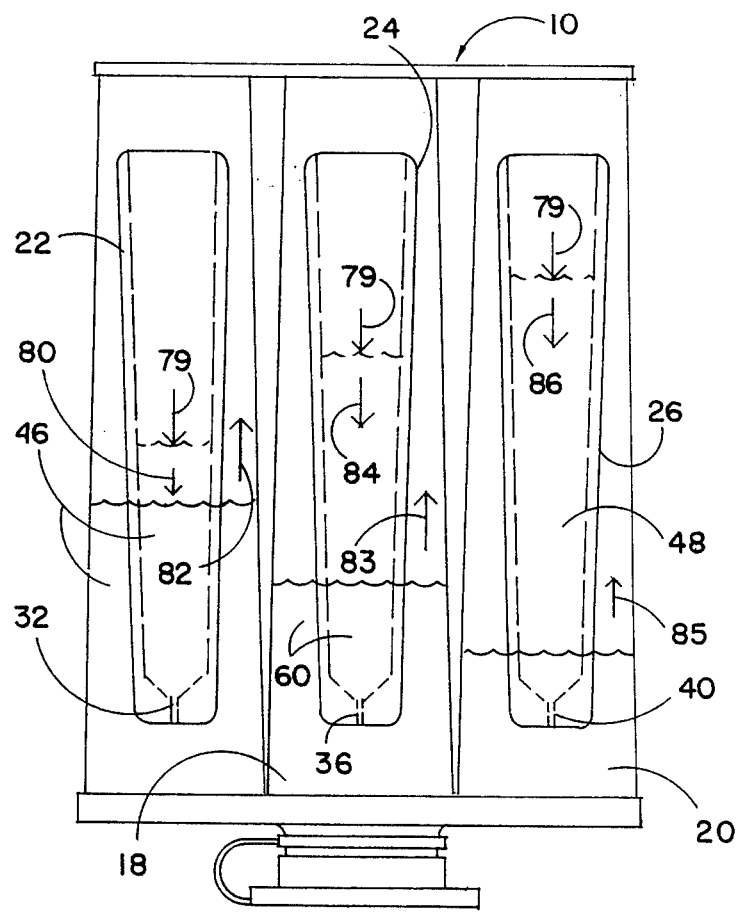
FIG. 3 is a front elevational view of the tester with reference, test and standard liquids descending in respective columns to provide a comparative viscosity test.

When apparatus 10 is positioned as described above the test commences. A pressure head 79, shown in FIG. 3, is created upon the liquid in each of the columns 22, 24 and 26. That pressure head is created because the level of liquid in the column is higher than the level outside of the column. The pressure head drives the liquid downwardly through the submerged orifice in the column and into that portion of the chamber outside of the column. Reference liquid 46 in first column 22 descends in the direction of arrow 80. The pressure head on the liquid in column 22 drives liquid 46 through orifice 32 so that the liquid level outside of the column rises in the direction of arrow 82 until it meets the level of liquid 46 within column 22. Similarly, liquid 60 in column 24 descends in the direction of arrow 84 as that liquid is driven through orifice 36. Liquid 60 outside of column 24 rises in the direction of arrow 83 until the liquid levels inside and outside of column 22 are equal. Liquid 48 in column 26 similarly descends in the direction of arrow 86 and liquid 48 is driven through orifice 40 so that the liquid level in chamber 20 rises in the direction of arrow 85 until it is equal to the liquid level in column 26. When pressure equilibrium is achieved, apparatus 10 again appears as shown in FIG. 1 and the test is completed.

As previously indicated, liquid 46 has a relatively low viscosity and liquid 48 possesses a relatively high viscosity. Accordingly, liquid 46 descends much more rapidly in column 22 than does liquid 48 in column 26 and during the test the liquid 48 maintains a higher level within its column. Liquid 60 descends in its column slower than does liquid 46, but faster than does liquid 48. Accordingly, at any given instant during the test the level of liquid 60 within column 24 is between the columnar levels of liquids 46 and 48. This indicates that liquid 60 has a viscosity which is greater than the viscosity of liquid 46 but less than the viscosity of liquid 48. Since liquid 46 represents the lowest acceptable viscosity and liquid 48 represents the highest acceptable viscosity, liquid 60 has an acceptable viscosity level. If, however, at any instant during the test the level of liquid 60 within column 24 drops below the level of liquid 46, or alternatively, is higher than the level of liquid 48, this indicates that liquid 60 has an unacceptable viscosity.

This comparative test proves extremely accurate because there is atmospheric interconnection between the channel within each column and the chamber and because each of the orifices remains submerged throughout the test. As a result, pockets of gas which can interfere with the test are not trapped beneath the descending fluid. Moreover, tapering the columns permits the liquid to descend within each column at a constant rate throughout the entire test. As a result, the relative liquid levels remain constant throughout the test so that a comparative measure of viscosity may be obtained at any instant during the descent. And, if a measurement is missed, the test can be quickly and simply repeated as many times as is required to obtain an accurate comparison.

Figure 5:
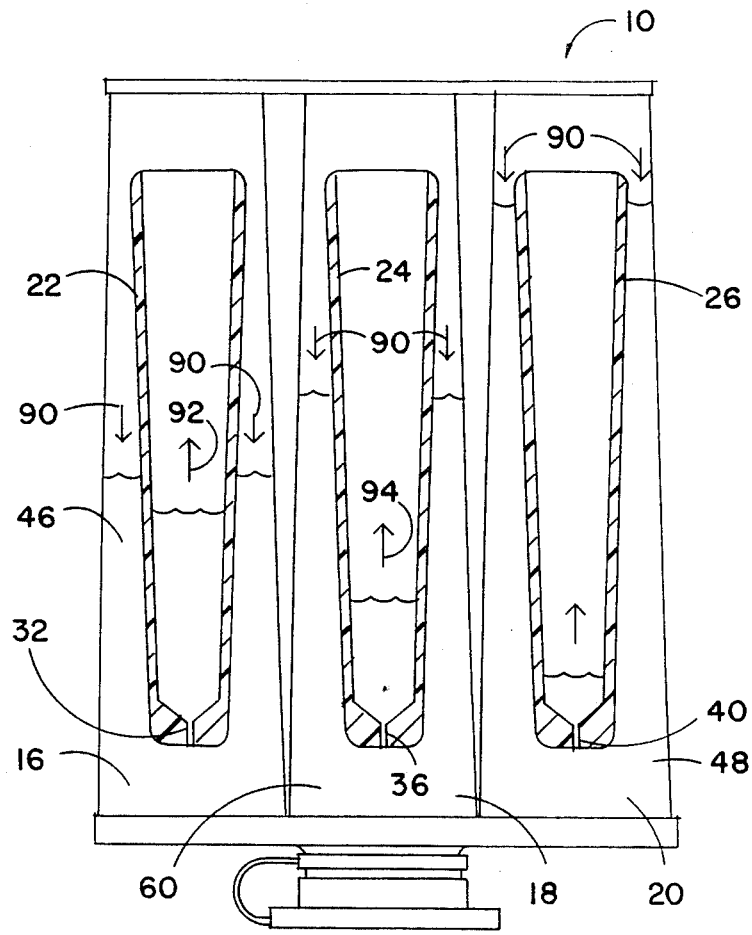
FIG. 5 is a front elevational partially sectional view of the tester with an ascending column test in progress.
Figure 4:
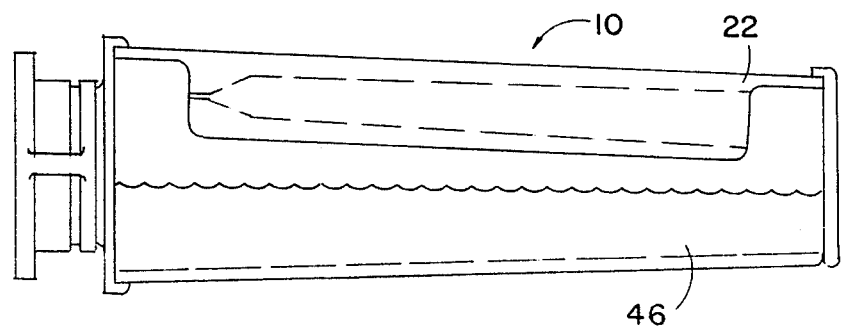
FIG. 4 is a side elevational view of the viscosity tester being tipped in the opposite direction so that ascending column comparative testing may be performed.

Alternatively, viscosity may be tested by comparing ascending liquid levels within the respective columns 22, 24 and 26. This test is conducted simply by tipping apparatus 10 in an opposite direction into the generally horizontal position shown in FIG. 4. In this case, the apparatus is tipped so that the liquid levels are below the columns. When apparatus 10 is again manipulated into the vertical position, shown in FIG. 5, the liquids 46, 60 and 48 are outside of their respective columns 22, 24 and 26. Resulting pressure heads, indicated by arrows 90, are created in each of the columns and these pressure heads drive the liquids 46, 60 and 48 through the respective orifices 32, 36 and 40 into columns 22, 24 and 26. Liquid 46 ascends in column 22 in the direction of arrow 92 until it reaches the liquid level in chamber 16 outside of the column. Similarly, liquid 60 ascends in the direction of arrow 94 within column 24 until it reaches the equilibrium level; and liquid 48 ascends in column 26 until its level reaches the liquid level outside of the column. During this ascent period, the liquid levels in the three columns may be compared at any given instant to determine relative viscosity. Because liquid 46 has the lowest viscosity it travels most rapidly up column 22. Conversely, because liquid 48 has the highest viscosity it travels most slowly up its respective column. Again, because liquid 60 has a viscosity which is intermediate that of liquids 46 and 48, its level remains between the levels of liquids 46 and 48 in columns 22 and 26, respectively. The viscosity of liquid 60 is unacceptable if the columnar level of liquid 60 is either greater than that of liquid 46 or less than that of liquid 48.

Figure 6:
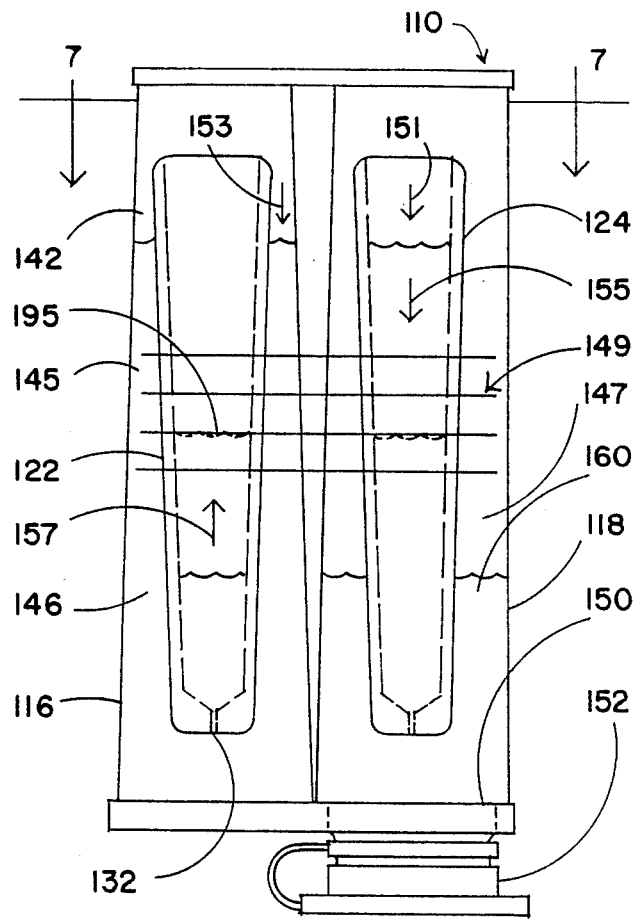
FIG. 6 is a front elevational view of an alternative viscosity tester for providing an absolute measure of viscosity.
Figure 7:
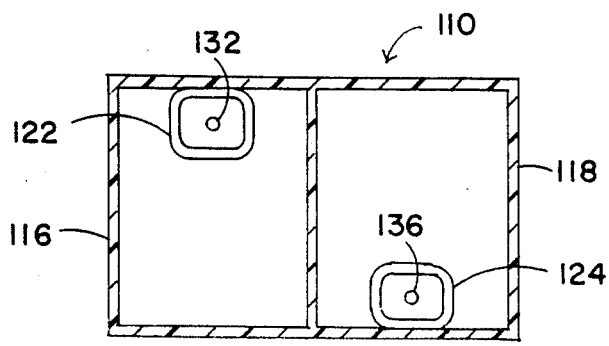
FIG. 7 is a cross sectional view taken along line 7—7 of FIG. 6.

In the alternative apparatus 110, shown in FIGS. 6 and 7, an absolute measure of viscosity may be obtained. Apparatus 110 includes a reference chamber 116 and a test chamber 118 that are constructed similarly to the chambers described in the previous embodiment. In this embodiment a third chamber is not required. A first column 122 is mounted to a rearward wall of chamber 116, and a similar column 124 is permanently mounted to the forward wall of chamber 118. As shown in FIG. 7, columns 122 and 124 may have a generally rectangular cross sectional shape, although this is not a limitation of the invention. In alternative embodiments the columns may have circular or other cross sectional shapes. Both the chambers 116 and 118 and the columns 122 and 124 are transparent so that liquid levels may be clearly monitored for tests using apparatus 110.

Reference chamber 116 is sealed and partially filled with a liquid 146 having a known viscosity and a nitrogen atmosphere 142 from which oxygen has been largely entirely removed. Again, this invention is particularly desirable for use in testing the viscosity of hydrocarbon fuels. In such cases, reference chamber 116 is partially filled with a predetermined hydrocarbon. The front face 145 of chamber 116 and the adjoining front face 147 of chamber 118 contain reference or indicator lines 149. These lines are utilized for providing an absolute measure of viscosity as described more fully below.

Chamber 118 includes an entrance through which test liquid 160 may be selectively introduced into and removed from the test chamber 118. A cap 152 is mounted as previously described for selectively covering entrance 150.

To perform absolute viscosity testing, cap 152 is opened and test liquid 160 having a viscosity/temperature characteristic that is the same as that of the reference liquid 146 is introduced into chamber 118. The liquid temperature within the respective chambers is allowed to equalize. Apparatus 110 is then tipped into a horizontal position, as described and shown in FIGS. 2 and 4, so that column 124 is entirely submerged beneath liquid 146. At the same time, column 122 in test chamber 118 is suspended above test liquid 160. Apparatus 110 is then manipulated back into the vertical position shown in FIG. 6. At this instant, test liquid 160 generally fills column 124. However, column 122 which has been suspended above reference liquid 146 is generally empty. This creates a pressure head 151 on the liquid 160 in column 124. At the same time, a pressure head 153 is created on reference liquid 146 outside of column 122. Pressure head 151 causes test liquid to descend in the direction of arrow 155 in column 124. This drives liquid 160 through orifice 136 in column 124 and the level of liquid 160 outside of column 124 rises. At the same time, pressure head 153 causes liquid 146 to be driven through orifice 132 into column 122. As a result, liquid 146 rises within the column in the direction of arrow 157. At a certain level, for example, at the level indicated by line 195, the ascending column of reference liquid 146 instantaneously equals the level of descending test liquid 160. That point provides an absolute measure of the viscosity of the test liquid.

The positions of indicator lines 149 are determined by calibrating apparatus 110. The viscosity of reference liquid 146 is known, and as a result, the rate at which liquid 146 ascends or descends within column 122 is known. By introducing various liquids having known viscosities into chamber 118, and running the above test with these two known liquids, the levels at which the ascending and descending columns cross may be determined for the various test liquid viscosities. Such levels are then marked by calibrated indicator lines 149.

The above absolute measurement test may be alternatively performed by tipping apparatus 110 in the opposite direction so that reference liquid 146 descend in column 122 and the test liquid 160 rises in column 124.

The apparatus of this invention enables viscosity to be quickly and accurately determined, even by relatively unsophisticated personnel. The device is uncomplicated to operate and is constructed of relatively durable and shock resistant materials. As a result, it is particularly convenient for use in the field.

Although specific features of the invention are shown in some drawings and not others, this is for convenience only as each feature may be combined with any or all of the other features in accordance with the invention.

Other embodiments will occur to those skilled in the art and are within the following claims:

What is claimed is:

1. A viscosity test apparatus comprising:
    a reference chamber partially filled by a predetermined volume of a reference liquid having a known viscosity;
    a test chamber attached to said reference chamber and including means for partially filling said test chamber with a test liquid having a volume and a viscosity/temperature characteristic that are substantially similar to those of said reference liquid;
    an elongate first conducting column including an open upper end that interconnects said reference chamber and said first column and a lower end having first orifice means that are submersible in said reference liquid for conducting said reference liquid under a pressure head between said first column and said reference chamber; and
    a second conducting column mounted within said test chamber in substantial alignment with said first column and having dimensions substantially identical to said first column, said second column including an open upper end that interconnects said test chamber and said second column, and a lower end having second orifice means that are submersible in said test liquid for conducting test liquid under a pressure head between said second column and said test chamber, said reference and test chambers being simultaneously manipulable to provide said reference and test liquids with respective pressure heads such that the respective levels of the reference liquid and said test liquid in said first and second columns may be compared instantaneously, to provide a measure of viscosity of said test liquid.

2. The apparatus of claim 1 in which said reference chamber is sealed.

3. The apparatus of claim 2 in which said reference chamber includes a nitrogen atmosphere from which oxygen has been substantially entirely removed.

4. The apparatus of claim 1 in which each said conducting column is tapered from its upper end to its lower end such that the liquid level in said column varies, under a pressure head, at a generally constant rate.

5. The apparatus of claim 1 in which each of said first and second orifice means include equal diameters.

6. The apparatus of claim 1 in which said reference chamber and said test chamber include first and second transparent portions, respectively, for viewing said first and second columns, and in which said first and second columns include third and fourth transparent portions, respectively, for viewing the instantaneous levels of said reference liquid and said test liquid in said first and second columns.

7. The apparatus of claim 1 in which said means for partially filling include an entrance into said test chamber and means for selectively covering said entrance to hold said test liquid in said test chamber.

8. The apparatus of claim 1 in which said test and reference liquids include hydrocarbons.

9. The apparatus of claim 1 further including a standard chamber attached to at least one of said reference chamber and said test chamber and being partially filled by a standard liquid having a volume and a viscosity/temperature characteristic that are substantially similar to those of said reference liquid, and a third conducting column mounted in said standard chamber in substantial alignment with said first and second columns and having dimensions substantially identical to said first and second columns, said third column including an open upper end that interconnects said standard chamber and said third column, and a lower end having third orifice means that are submersible in said standard liquid for conducting standard liquid under a pressure head between said third column and said standard chamber, said standard chamber being simultaneously manipulable with said reference and test chambers to provide said reference, test and standard liquids with pressure heads for driving said reference, test and standard liquids through said first, second and third orifices, respectively, such that the levels of said liquids in said column may be instantaneously compared to provide a measure of the viscosity of said test liquid relative to said reference and standard liquids.

10. The apparatus of claim 9 in which said standard chamber is sealed.

11. The apparatus of claim 10 in which said standard chamber includes a nitrogen atmosphere from which oxygen has been substantially entirely removed.

12. The apparatus of claim 9 in which said third column is tapered from its upper end to its lower end such that the liquid level in said third column varies, under a pressure head, at a generally constant rate.

13. The apparatus of claim 9 in which said third orifice means includes a diameter equal to that of said first and second orifices.

14. The apparatus of claim 9 in which said standard chamber includes first transparent means for viewing said third column and in which said third column includes second transparent means for viewing the level of standard liquid in said third column.

15. The apparatus of claim 9 in which said standard liquid includes a hydrocarbon.

16. The apparatus of claim 1 in which said first and second columns are attached respectively to forward and rearward walls of said reference and test chambers such that one of said reference and test liquids descends under a pressure head within its respective column, and the other of said reference and test liquids ascends under a pressure head within its respective column.

17. The apparatus of claim 16 in which said reference and test chambers include means for indicating when the respective fluid levels in said first and second columns are instantaneously equal to provide a measure of the absolute viscosity of said test liquid.

* * * * *